(12) United States Patent
Kreuzer et al.

(10) Patent No.: US 6,876,474 B2
(45) Date of Patent: Apr. 5, 2005

(54) METHOD FOR TRACKING PARTICLES AND LIFE FORMS IN THREE DIMENSIONS AND IN TIME

(75) Inventors: H. Juergen Kreuzer, Portuguese Cove (CA); Manfred H. Jericho, Herring Cove (CA)

(73) Assignee: Dalhousie University, Halifax (CA)

( * ) Notice: Subject to any disclaimer, the term of this patent is extended or adjusted under 35 U.S.C. 154(b) by 0 days.

(21) Appl. No.: 10/721,074

(22) Filed: Nov. 26, 2003

(65) Prior Publication Data

US 2004/0169903 A1 Sep. 2, 2004

Related U.S. Application Data

(60) Provisional application No. 60/429,355, filed on Nov. 27, 2002.

(51) Int. Cl.[7] .................................................. G03H 1/26
(52) U.S. Cl. ............................................. 359/22; 359/9
(58) Field of Search ........................... 359/1, 9, 10, 22, 359/29, 32, 35; 378/36, 87; 382/279, 280

(56) References Cited

U.S. PATENT DOCUMENTS 5,548,419 A * 8/1996 Adrian et al. ................. 359/24
6,411,406 B1 6/2002 Kreuzer ........................ 359/10
6,535,276 B2 * 3/2003 Dubois ....................... 356/28.5

OTHER PUBLICATIONS

Book, Principles of Optics seventh (Expanded) Edition by Max Born and Emil Wolf, Cambridge University Press 1999, pp. 412 to 417 and 645 to 652.

Book, Handbook of Holographic Interferometry, Thomas Kreis, Wiley Jan. 2005, Table of Contents –sections 3.2 to 3.4.

* cited by examiner

Primary Examiner—Leo Boutsikaris

(57) ABSTRACT

A method for tracking particles and life forms in three dimensions and in time. The present invention applies a numerical reconstruction approach to digital in-line holographic microscopy images in order to generate a time sequence hologram representing the trajectory of objects such as particles and life forms. By subtracting consecutive (in time) holograms of a particle sample volume and then adding the resulting differences, a final hologram is constructed that contains the time evolution of the object trajectory free from spurious background interference effects.

5 Claims, 3 Drawing Sheets

FIGURE 1A
FIGURE 1C
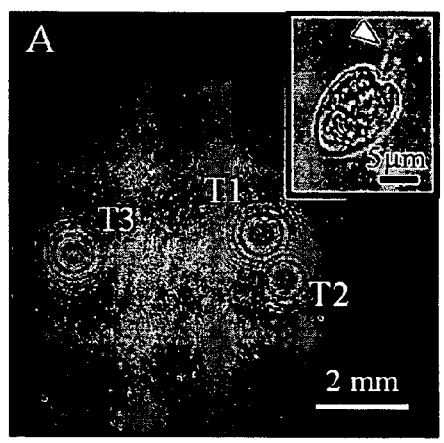
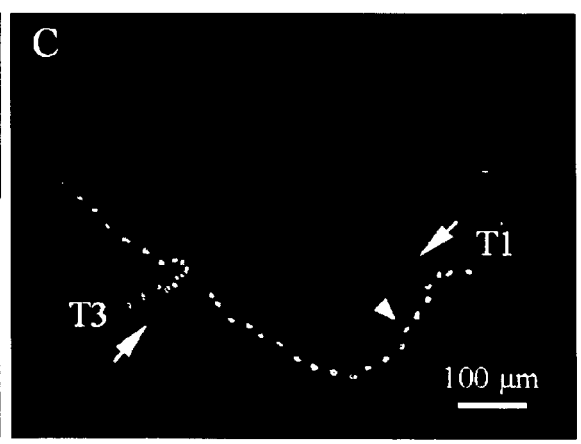
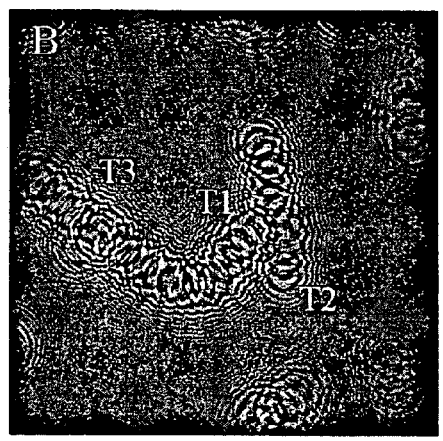
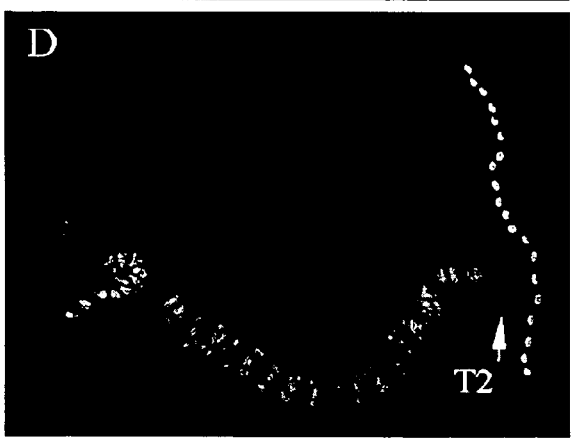
FIGURE 1B
FIGURE 1D

FIGURE 2A
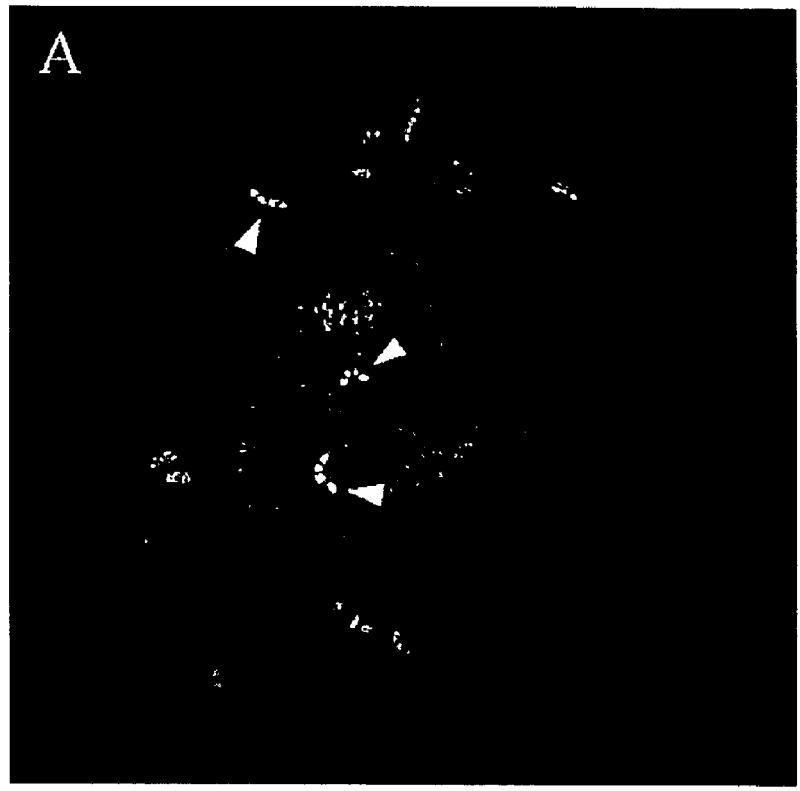
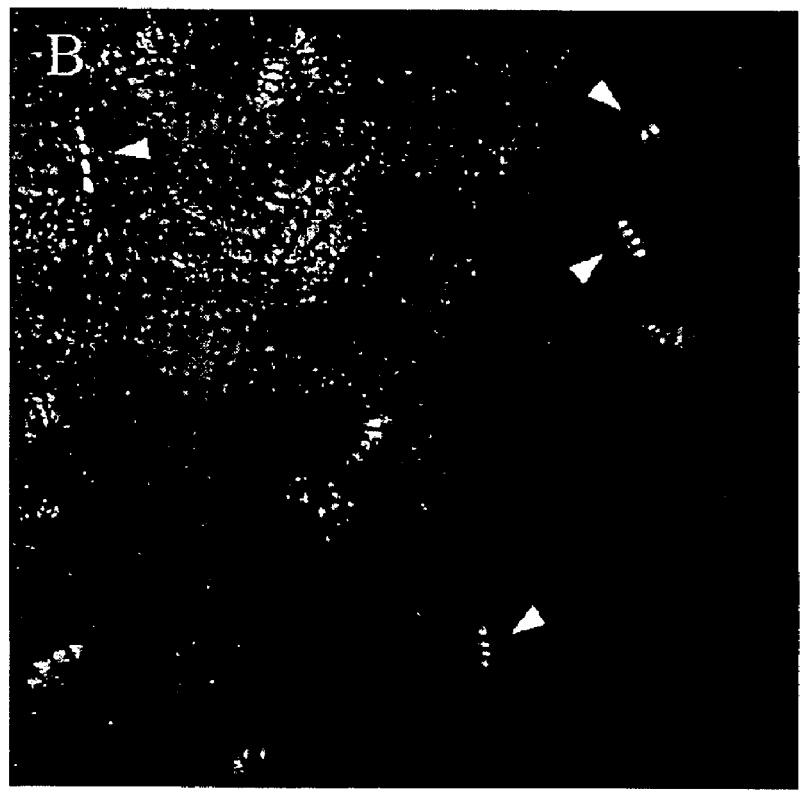
FIGURE 2B

METHOD FOR TRACKING PARTICLES AND LIFE FORMS IN THREE DIMENSIONS AND IN TIME

CROSS-REFERENCE TO RELATED APPLICATION

This application claims priority from U.S. Provisional Patent Application Ser. No. 60/429,355, filed Nov. 27, 2002, the entirety of which is incorporated herein by reference.

FIELD OF INVENTION

The present invention relates to the field of holographic microscopy. In particular, to a method for tracking the trajectories of particles in three dimensions and in time using digital in-line holography.

BACKGROUND

The efficient recording of the trajectories of micron size particles that are moving throughout a three dimensional (3-D) space has been an important problem in several branches of science such as colloidal suspensions, the motion of algae or larvae in water, the motion of bacteria around and in cells, and the characterization of marine particulates.

One approach to tracking such particles has been the use of compound light microscopy. Conventional compound light microscopy can give high-resolution information about an object but only in a single focal plane. Therefore, compound light microscopy is effectively limited to two dimensional tracking of particles.

Digital in-line holography (DIH) offers a rapid and efficient approach to construct high-contrast 3-D images of a sample volume from a single hologram. An exemplary approach to DIH is described in U.S. Pat. No. 6,411,406 issued Jun. $25^{th}$, 2002 to H. Juergen Kreuzer which is incorporated in its entirety herein by reference. In digital in-line holography a spherical wave, emanating from a "point" source of linear dimensions of the order of the wavelength, illuminates an object, typically at a distance of a few thousand wavelengths from the source, and forms a highly magnified diffraction pattern on a screen much further away. Details of DIH and a thorough discussion of its history and potential have been presented in a number of publications together with earlier results in such diverse areas as cell biology, micro-particle imaging and tracking, and polymer crystallization.

Holography is a two-step process: first, a hologram must be recorded, and second, it must be reconstructed to yield an "image" of the object. In DIH the hologram is recorded by a detector array, such as a charge-coupled device (CCD) camera for detecting photons, and the frame (i.e. the detector recorded hologram) is then captured by a computer in which the reconstruction is done using numerical means. The role of reconstruction is to obtain the three-dimensional structure of the object from the two-dimensional hologram on the screen (i.e. the detector array), or, in physical terms, to reconstruct the wave front at the object. This can be achieved via a Kirchhoff-Helmholtz transform such as that represented in Equation 1.

$$K(\vec{r}) = \int_S d^3\xi \vec{I}(\vec{\xi}) \exp[2\pi i \vec{\xi} \cdot \vec{r}/\lambda \xi] \quad (1)$$

In the Kirchhoff-Helmholtz transform represented in Equation 1, the integration extends over the two dimensional surface of the screen (assumed to be perpendicular to the optical axis) with coordinates $\xi=(X,Y,L)$, where L is the distance from the source (pinhole) to the center of the screen (detector array) and $I(\xi)$ is the contrast image (hologram) on the screen, obtained by subtracting the images with and without the object present. The function K(r) is significantly structured and differs from zero only in the space region occupied by the object. By reconstructing the wave front K(r) on a number of planes at various distances from the source in the vicinity of the object, a three-dimensional image can be built up from a single two-dimensional hologram. K(r) is a complex function and one usually plots its magnitude to represent the object, although phase images are also available. For the numerical implementation of the transform a fast algorithm that evaluates K(r) without any approximations can be used. The algorithm employs a coordinate transformation that transforms the integral into a convolution that is solved by three consecutive Fast Fourier Transforms.

In holography, the term 'reconstruction' is used to describe obtaining the function K(r) from the hologram. The plot of |K(r)| on a two-dimensional plane perpendicular to the optical axis, is called a two dimensional (2-D) holographic reconstruction, is equivalent to a single in-focus image taken in a conventional compound microscope. In DIH a stack of 2-D holographic reconstructions can be generated from a single hologram. Combining such a stack results in a three-dimensional image of the object; this latter step is usually referred to as 3-D reconstruction.

The input to the 3-D reconstruction as represented, for example, by equation (1) is the contrast image for a perfectly spherical incoming wave. Perfecting this image is the hardest part in the practical implementation of DIH. The normal procedure for generating the contrast image is as follows: (i) Record digitally the hologram of the object, i.e. the intensity matrix, $I_{nm}$, recorded on the detector array, where n and m enumerate pixels in the x- and y-axis. (ii) Remove the object and record digitally the intensity matrix of the illuminating laser. (iii) Subtract the results of (ii) from the results of (i) to numerically construct the contrast image, corrected for the intensity variations in the primary laser beam. Using this procedure almost all imperfections in the laser source are eliminated. Indeed, this procedure minimizes the quality requirements on the laser itself, as long as the laser is sufficiently stable to identically capture both images.

In many situations it may not be possible or convenient to remove the object from the optical path in order to construct the contrast image. This is clearly the case when the object is in motion and it is desired to record the time evolution of the object's trajectory.

What is needed is an effective approach for tracking the trajectories of particles and life forms that are moving throughout a three dimensional space.

SUMMARY OF INVENTION

The present invention is directed to a method for tracking particles and life forms in three dimensions and in time. The present invention applies a numerical reconstruction approach to digital in-line holographic microscopy images in order to generate a time sequence hologram representing the trajectory of objects such as particles and life forms.

By subtracting consecutive (in time) holograms of a particle suspension and then adding the resulting differences, a final data set (hologram) is constructed that contains the time evolution of the object trajectory free from spurious background interference effects.

A method according to the present invention provides for the removal of a) distortions or deviations from a theoretically perfect spherical wave front from an illuminating laser, b) distortions due to an imperfect pinhole, and c) other optical/image interference caused by dust, background, noise etc. This requires the generation of two holographic images, one with a subject present, the second with the subject either in a new position or absent. The first image is then subtracted from the second such as to generate a 'background free' image containing only (i.e. isolating) the subject, which can then be reconstructed via mathematical formulae such as, for example, those described in U.S. Pat. No. 6,411,406 issued Jun. 25$^{th}$, 2002 to H. Juergen Kreuzer.

A method according to the present invention further provides for tracking of the subject via the repeated subtraction of every second image from a previous image in a series of N time-spaced images, such as to generate a series of N/2 time-spaced holographic images (e.g. $(h_1-h_2)$, $(h_3-h_4)$, . . . , $(h_{n-1}-h_n)$) that contain only the subject.

A method according to the present invention further provides for adding (combining) of the series of N/2 time-spaced images together to generate a single holographic image that contains the images of the subjects at all positions in time represented in the full series of N time-spaced images. Numerical reconstruction is then performed on the single combined holographic image at each of a plurality of reconstruction planes. The reconstruction for a given reconstruction plane results in a view of the positions of all subjects, in all time-spaced images, that were ever present in that plane. For a subject that, for example, moves only horizontally within the reconstruction plane in the time-spaced images, the reconstructed image will effectively display its trajectory (i.e. its successive locations over the full time-period represented by the N time-spaced images).

Alternatively, a method according to the present invention can use algorithms, for generating the series of time spaced holograms, other than the subtraction of every second image (i.e. $(h_1-h_2)$, $(h_3-h_4)$, . . . , $(h_{n-1}-h_n)$) algorithm. For example, a single image can be subtracted from a succession of time spaced images (e.g. $(h_2-h_1)$, $(h_3-h_1)$, $(h_4-h_1)$ . . . $(h_n-h_1)$) to derive the series of time spaced images. Such an embodiment is particularly useful when the subject is moving slowly in which case the embodiment in which every second image is subtracted from the preceding image could cause the elimination of a part or all of the subject in a resulting difference image.

In accordance with one aspect of the present invention, method for tracking the trajectory in three-dimensions and in time of an object in a sample volume comprising the steps of: a) recording a time-spaced sequence of digital in-line holograms, generating a sequence of N holograms; b) subtracting from a first hologram a second hologram in each successive pair of the sequence of N holograms to generate N/2 difference holograms; c) summing the N/2 difference holograms to generate a summed hologram; and d) reconstructing images of the object at a plurality of depths into the sample volume representing the trajectory of the object.

In accordance with another aspect of the present invention, a method for tracking the trajectory in three-dimensions and in time of an object in a sample volume comprising the steps of: a) recording a time-spaced sequence of digital in-line holograms, generating a sequence of N holograms; b) subtracting a first hologram from each of the remaining holograms of the sequence of N holograms to generate N−1 difference holograms; c) summing the N−1 difference holograms to generate a summed hologram; and d) reconstructing images of the object at a plurality of depths into the sample volume representing the trajectory of the object.

In accordance with still another aspect of the present invention, a method for tracking the trajectory in three-dimensions and in time of an object in a sample volume comprising the steps of: a) recording a time-spaced sequence of digital in-line holograms, generating a sequence of N holograms; b) subtracting a first hologram from each of the remaining holograms of the sequence of N holograms to generate N−1 difference holograms; c) reconstructing an image of the object at a depth into the sample volume for each of the N−1 difference holograms, generating N−1 subject images; and d) combining the N−1 subject images to generate a 3-D image representing the trajectory of the object.

In accordance with yet another aspect of the present invention, a method for tracking the trajectory in three-dimensions and in time of a plurality of objects in a sample volume comprising the steps of: a) recording a digital in-line hologram as a first series of pixels in a buffer; b) for a subsequent time-spaced sequence of digital in-line holograms, recording each hologram represented as a second series of pixels by: i) subtracting each pixel in the second series of pixels from a corresponding pixel in the buffer, for a hologram having an even ordinal number in the sequence of digital in-line holograms and ii) adding each pixel in the second series of pixels to a corresponding pixel in the buffer, for a hologram having an odd ordinal number in the sequence of digital in-line holograms; and c) reconstructing images of the object at a plurality of depths into the sample volume representing the trajectory of the object.

Other aspects and features of the present invention will become apparent to those ordinarily skilled in the art to which it pertains upon review of the following description of specific embodiments of the invention in conjunction with the accompanying figures.

BRIEF DESCRIPTION OF DRAWINGS

The present invention will be described in conjunction with the drawings in which:

FIGS. 1A–D illustrate holograms and reconstructed trajectories, according to the present invention, of the alga *Tetraselmis* in sea-water using a DIH approach.

FIGS. 2A–B illustrate reconstructed trajectories, according to the present invention, of the alga *Tetraselmis* in seawater from four individual holograms using a DIH approach.

DETAILED DESCRIPTION

Figure 3:
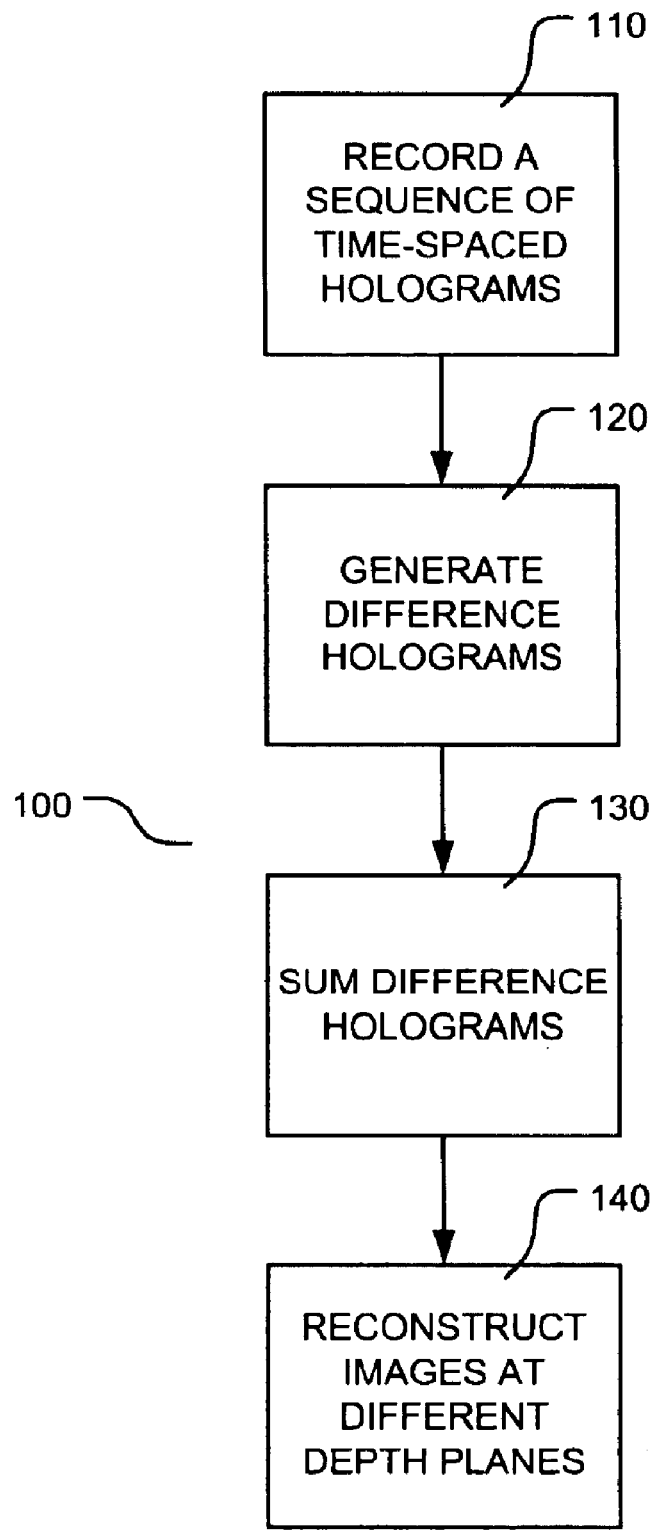
FIG. 3 is a flow chart of the steps in an exemplary embodiment of a method according to the present invention.

Applying a digital in-line holography approach using a detector array having a fast capture rate, it is possible to record digitally the motion of particles in a sample volume from their successive positions in time. Subsequently images at selected depths can be reconstructed so that the trajectory and speed of a collection of particles can be captured as 3-D data sets. To illustrate a method according to the present invention, holographic images were recorded (see FIG. 1A described below) of a live culture of the single-celled marine flagellate *Tetraselmis*, contained in a 1 mm thick layer of salt water between a microscope slide and a cover slip. These algae are flattened and propel themselves by four anterior flagella.

FIGS. 1A–D illustrate holograms and reconstructed trajectories, according to the present invention, of the alga *Tetraselmis* in sea-water using a DIH approach (Blue laser, 1 μm pinhole, source to sample distance 2.5 mm, source to CCD camera distance 20 mm.). FIG. 1A illustrates a single hologram of three algae (T1–T3) with an inset bright-field image of single alga, showing flagella (arrowhead); (Zeiss, Plan-Neofluar 100×/1.30 oil). FIG. 1B illustrates a sum of 10 difference holograms (from a total of 20) of the trajectories of the algae in FIG. 1A. FIG. 1C illustrates a reconstruction of the summed hologram of FIG. 1B in one plane with the trajectory of alga T1 in focus. FIG. 1D illustrates a reconstruction from the hologram of FIG. 1B in a plane 500 μm above that in FIG. 1C. Arrows indicate the directions of algal motion.

FIGS. 2A–B illustrate reconstructed trajectories, according to the present invention, of the alga *Tetraselmis* in seawater from four individual holograms using a DIH approach (Blue laser, 1 μm pinhole, source to CCD camera distance 3.05 cm, reconstruction area 1×1 mm$^2$). In FIG. 2A arrows mark three algae that are in sharp focus in a plane 2.4 mm from the pin-hole. In FIG. 2B arrows mark four algae in sharp focus in a plane 6.7 mm from the pin-hole. In both FIGS. 2A and 2B several less sharply reconstructed algae trajectories are also visible. Sets of closely spaced reconstruction planes thus allow the determination of algae density throughout volumes several cm$^3$ in size. Analysis of the sample illustrated in FIGS. 2A–B through multiple reconstructions has shown that this sample contained 96 algae in a volume of about 1 mm$^3$ of sea-water.

FIG. 3 is a flow chart of the steps 100 in an exemplary embodiment of a method according to the present invention. To obtain high-resolution DIH reconstruction images of the movement trajectories of an object (e.g. a particle or a life form), an exemplary embodiment of a method according to the present invention begins with a step 110 of recording a sequence N of time-spaced holograms ($h_1, \ldots, h_N$). This is followed by a step 120 of removing undesired background effects (such as the set of large concentric rings in FIG. 1A) thereby isolating the object by, for example, subtracting consecutive hologram pairs, pixel by pixel, to generate difference holograms, i.e. ($h_1-h_2$), ($h_3-h_4$), etc. Next in a step 130 the resultant difference holograms (i.e. ($h_1-h_2$), ($h_3-h_4$), etc.) are summed into a single summed hologram. The summed hologram contains all holograms in the sequence with the sign alternated for each successive (alternate) hologram. Preferably the summed hologram has the same size as any single original hologram. Subtracting alternate holograms preferably ensures that the dynamic range of the numerical processing means is not exceeded and that only the object-related-information is retained. In a step 140 the summed hologram is reconstructed using, for example, a Kirchhoff-Helmholtz transform (see Equation 1) to obtain images at reconstruction planes at different depths in the sample volume. Such images show the sequential positions at successive recording times of the object contained in the sample volume.

FIGS. 1C and 1D show the trajectories of three algae in two such reconstructions in two planes separated by 500 μm. Twenty sequential positions clearly define the trajectory of alga T1 (FIG. 1A), which swims in a zigzag fashion more or less confined to a plane parallel to the glass slide. It also rotates about the long axis, the flattened shape alternately imaged edge on (triangle: FIG. 1C) or en face (the two preceding images). Access to 3-D information in holographic imaging, according to the present invention, is particularly well illustrated by alga T3 (FIG. 1C). This alga comes to lie in the reconstruction plane but earlier images are progressively out of focus, indicating that the direction of motion had a large component perpendicular to the reconstruction plane. To obtain the complete trajectory, further reconstructions from the same hologram file can be made in as many planes as necessary without the need for recording further holograms. Reconstructed in one plane (FIG. 1C), the trajectory of alga T2 is visible, only severely out of focus, but becomes clearly visible when the hologram in FIG. 1B is reconstructed in a plane that lies 500 μm higher, FIG. 1D. From the reconstructions an average algal swimming speed of approximately 150 μm/s was obtained.

A method according to the present invention is not limited to the sampling of small volumes. FIGS. 2A–B show an example where algae were imaged in several cm$^3$ of water contained in a rectangular spectrometer optical cell. FIGS. 2A–B illustrate how a method according to the present invention can be used to determine the distribution of moving particles in a suspension. For the images in FIGS. 2A–B only four separate holograms were recorded. FIG. 2A shows the short trajectories of several algae (marked by arrows) that lie in the reconstruction plane. Other, out of focus, trajectories are also visible in the image. Representation of a particle by a short trajectory instead of a single spot made it easier to identify the algae. In FIG. 2B the same data set shows algae in a plane 4.3 mm away from the plane of FIG. 2A. Volumes of several cm$^3$ can be examined easily in this manner.

In an exemplary embodiment of a method according to the present invention removal of background effects and reconstruction of a summed hologram are easily accomplished so that high-resolution tracking of many particles in 4-D (3-D and time) from just a single hologram data set can be performed. Since resolutions on the order of the wavelength of light have been achieved with DIH, tracking of organisms as small as bacteria, the motion of plankton in water and micro-particles in fluid flow have also been performed. At lower resolution, the aerial trajectories of flying insects should be possible.

When a holographic image is subtracted from the previous image in the time-spaced series e.g. ($h_3-h_4$), the resultant single image effectively contains two images of each single subject, one positive and one negative, with any background or image data common to both images removed. The resulting N/2 images have N subject positions recorded in the N/2 images.

In the above described algorithm (i.e. subtraction of every other image), if a subject does not move or change between the two images (i.e. is identical in both images) it will be removed. That is, there will be no image of the subject shown at that position in the resultant reconstructed track image. In an alternative embodiment of a method according to the present invention, this limitation can be overcome by subtracting a later image in the sequence instead of the immediately next image, for example ($h_1-h_4$), ($h_2-h_5$), ($h_3-h_6$), ($h_7-h_{10}$), ($h_8-h_{11}$), ($h_9-h_{12}$). The increased time spacing between the subtracted images increases the possibility of movement between the subtracted images. The N/2 images are added together to derive the single holographic image. Reconstruction can be performed at each depth to derive the track images at each depth. In practice, the first position of a subject is always seen and known, and positions where a subject is stationary can be inferred from the multiple positions shown for other subjects.

In an alternative embodiment of a method according to the present invention, a single image can be subtracted from a succession of time spaced images (e.g. $(h_2-h_1)$, $(h_3-h_1)$, $(h_4-h_1)$ ... $(h_n-h_1)$) to derive the series of time spaced images.

In another alternative embodiment of a method according to the present invention, reconstruction can be preformed, for a given depth, on each of the plurality of difference holograms to generate subject images. The subject images can then be combined together to generate a 3-D image representing the sequential positions at successive recording times of the object contained in the sample volume.

The summing of the successive subtracted pairs causes the individual pixel values in the final single summed hologram to remain 'within bounds' (i.e. prevents data overflow e.g. $(h_1-h_2)+(h_3-h_4)+(h_5-h_6)+(h_7-h_8)=h_1-h_2+h_3-h_4+h_5-h_6+h_7-h_8$). In an alternative embodiment of a method according to the present invention, each successive image can be 'added' to a summed image with a sign reversal for every other 'addition'. It is therefore not necessary to retain the previous image for summing purposes—the pixels of the next image in the series are merely added to or subtracted from the pixels of the summed image.

A method, according to the present invention, for tracking the three-dimensional movement of particles and minute life forms in time provides a single summed holographic image, containing the full 3-D movement of many objects in a sample volume over the same time period. This facilitates the study of how interactions and relationships between particles affect the trajectories and movements. It is also extremely useful for the study of such subjects as bacteria attacking cells as the full movement of the bacteria in three-dimensions can be studied in the one sequence of time-spaced images all summed to create one holographic image.

It will be apparent to one skilled in the art that numerous modifications and departures from the specific embodiments described herein may be made without departing from the spirit and scope of the present invention.

What is claimed is:

1. A method for tracking the trajectory in three-dimensions and in time of an object in a sample volume comprising the steps of:
    a) recording a time-spaced sequence of digital in-line holograms of the sample volume, generating a sequence of N holograms;
    b) in each successive pair of holograms in the sequence of N holograms, subtracting from a first hologram in the pair a second hologram in the pair to generate N/2 difference holograms;
    c) summing the N/2 difference holograms to generate a summed hologram; and
    d) numerically reconstructing images of the object at a plurality of depths into the sample volume representing the trajectory of the object from the summed hologram.

2. A method for tracking the trajectory in three-dimensions and in time of an object in a sample volume comprising the steps of:
    a) recording a time-spaced sequence of digital in-line holograms of the sample volume, generating a sequence of N holograms;
    b) subtracting a first hologram, selected from the sequence of N holograms, from each of the remaining holograms of the sequence of N holograms to generate N−1 difference holograms;
    c) summing the N−1 difference holograms to generate a summed hologram; and
    d) numerically reconstructing images of the object at a plurality of depths into the sample volume representing the trajectory of the object from the summed hologram.

3. A method for tracking the trajectory in three-dimensions and in time of an object in a sample volume comprising the steps of:
    a) recording a time-spaced sequence of digital in-line holograms of the sample volume, generating a sequence of N holograms;
    b) subtracting a first hologram, selected from the sequence of N holograms, from each of the remaining holograms of the sequence of N holograms to generate N−1 difference holograms;
    c) numerically reconstructing an image of the object at a depth into the sample volume for each of the N−1 difference holograms, generating N−1 subject images; and
    d) combining the N−1 subject images to generate a 3-D image representing the trajectory of the object.

4. A method for tracking the trajectory in three-dimensions and in time of a plurality of objects in a sample volume comprising the steps of:
    a) recording a time-spaced sequence of digital in-line holograms of the sample volume;
    b) generating a summed hologram by representing each hologram in the time-spaced sequence of digital in-line holograms as a series of pixels corresponding to the summed hologram and:
    subtracting each pixel in the series of pixels from a corresponding pixel in the
    summed hologram, for a hologram having an even ordinal number in the
    sequence of digital in-line holograms; and
    adding each pixel in the series of pixels from a corresponding pixel in the summed hologram, for a hologram having an odd ordinal number in the sequence of digital in-line holograms; and
    c) numerically reconstructing images of the plurality of objects, at a plurality of depths into the sample volume, representing the trajectories of the objects, from the summed hologram.

5. The method of any one of claims 1 to 4, wherein the step of reconstructing uses a Kirchhoff-Helmholtz transform to obtain image at a reconstruction plane for each of the plurality of depths in the sample volume.

* * * * *

UNITED STATES PATENT AND TRADEMARK OFFICE
CERTIFICATE OF CORRECTION

PATENT NO. : 6,876,474 B2
DATED : April 5, 2005
INVENTOR(S) : Kreuzer, H. Juergen et al.

It is certified that error appears in the above-identified patent and that said Letters Patent is hereby corrected as shown below:

<u>Column 8,</u>
Lines 38-42, should be continuous and read as follows:
 -- subtracting each pixel in the series of pixels from a corresponding pixel in the summed hologram, for a hologram having an even ordinal number in the sequence of digital in-line holograms; and --.
Line 53, "to obtain image" should read -- to obtain an image --.

Signed and Sealed this

Eighth Day of November, 2005

JON W. DUDAS
*Director of the United States Patent and Trademark Office*